United States Patent
Gers-Barlag et al.

(10) Patent No.: US 6,423,302 B1
(45) Date of Patent: Jul. 23, 2002

(54) USE OF OCTOCRYLENE FOR SOLUBILIZING 2,4-BIS{[4-(2-ETHYL-HEXYLOXY)-2-HYDROXY]-PHENYL}-6-(4-METHOXYPHENYL)-1,3,5-TRIAZINE IN COSMETIC OR DERMATOLOGICAL LIGHT PROTECTION COMPOSITIONS

(75) Inventors: Heinrich Gers-Barlag, Kummerfeld; Anja Müller, Rümpel, both of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/514,558

(22) Filed: Feb. 28, 2000

(30) Foreign Application Priority Data

Mar. 10, 1999 (DE) .......................... 199 10 477

(51) Int. Cl.⁷ .................... A61K 7/42; A61K 7/44; A61K 31/53; A61K 7/00
(52) U.S. Cl. .................. 424/59; 424/60; 424/400; 424/401; 514/241
(58) Field of Search ............... 424/59, 60, 400, 424/401

(56) References Cited

U.S. PATENT DOCUMENTS

| 5,605,679 A | 2/1997 | Hansenne et al. |
| 5,968,481 A | 10/1999 | Ascione et al. |

FOREIGN PATENT DOCUMENTS

| EP | 685221 | 12/1995 |
| EP | 0 775 698 A1 | 6/1997 |
| EP | 821941 | 2/1998 |
| EP | 845260 | 6/1998 |
| WO | WO 99/08653 | 2/1999 |

*Primary Examiner*—Shelley A. Dodson
(74) *Attorney, Agent, or Firm*—Norris McLaughlin & Marcus

(57) ABSTRACT

Use of ethylhexyl 2-cyano-3,3-diphenylacrylate (octocrylene) for solubilizing 2,4-bis-{[4-(2-ethylhexyloxy)-2-hydroxy]phenyl}-6-(4-methoxyphenyl)-1,3,5-triazine in cosmetic or dermatological light protection formulations.

20 Claims, No Drawings

USE OF OCTOCRYLENE FOR SOLUBILIZING 2,4-BIS{[4-(2-ETHYL-HEXYLOXY)-2-HYDROXY]-PHENYL}-6-(4-METHOXYPHENYL)-1,3,5-TRIAZINE IN COSMETIC OR DERMATOLOGICAL LIGHT PROTECTION COMPOSITIONS

The present invention relates to light protection formulations, in particular to cosmetic and dermatological light protection compositions.

The harmful effect of the ultraviolet part of sun radiation on the skin is generally known. While rays with a wavelength of less than 290 nm (the UV-C region) are absorbed by the ozone layer in the earth's atmosphere, rays in the region between 290 nm and 320 nm, the UV-B region, cause erythema, simple sunburn or even burns of greater or lesser severity.

A maximum erythema activity of sunlight is given as the narrower region around 308 nm.

Numerous compounds for protecting against UV-B radiation are known; these are derivatives of 3-benzylidenecamphor, 4-aminobenzoic acid, cinnamic acid, salicylic acid, benzophenone and also 2-phenylbenzimidazole.

It is also important to have available filter substances for the region between about 320 nm and about 400 nm, the UV-A region, since the rays of this region can also cause damage. For a long time it was incorrectly assumed that the long-wave UV-A radiation with a wavelength between 320 nm and 400 nm has only a negligible biological action and that, accordingly, the UV-B rays are responsible for most light-induced damage to human skin. However, in the meantime numerous studies have shown that UV-A radiation is much more harmful than UV-B radiation with regard to the triggering of photodynamic, specifically phototoxic, reactions and chronic changes in the skin. The harmful effect of UV-B radiation can also be intensified by UV-A radiation.

Thus, it has inter alia been found that even UV-A radiation, under quite normal everyday conditions, is sufficient to damage, within a short time, the collagen and elastin fibres, which are of essential importance for the structure and strength of the skin. This results in chronic light-induced changes in the skin—the skin "ages" prematurely. The clinical manifestation of light-aged skin includes, for example, wrinkles and lines, and also an irregular, furrowed relief. In addition, the areas affected by light-induced skin ageing can have irregular pigmentation. The formation of brown spots, keratoses and even carcinomas or malignant melanomas is also possible. Skin which has been prematurely aged as a result of everyday UV stress is further characterized by a lower activity of the Langerhans' cells and slight, chronic inflammation.

Approximately 90% of the ultraviolet radiation which reaches the earth consists of UV-A rays. Whilst the UV-B radiation varies widely depending on numerous factors (e.g. time of year and day or degree of latitude), the UV-A radiation remains relatively constant day after day irrespective of the time of year and day or geographical factors. Additionally, the majority of the UV-A radiation penetrates the living epidermis, whilst about 70% of the UV-B rays are held back by the horny layer.

Preventive protection against UV-A rays, for example by applying light protection filter substances in the form of a cosmetic or dermatological formulation to the skin, is therefore of fundamental importance.

Generally speaking, the light absorption behaviour of light protection filter substances is very well known and documented, not least because most industrialized countries have positive lists for the use of such substances, which impose very strict standards on the documentation. For the concentration of the substances in the finished formulations, the absorbance values can at best be a guide, since interaction with substances within the skin or with the surface of the skin itself may result in imponderables. In addition, it is usually difficult to estimate beforehand how uniformly and thickly the filter substance is distributed in and on the horny layer of the skin.

To test the UV-A protection performance, use is usually made of the IPD method (IPD≡immediate pigment darkening). Similarly to the determination of the light protection factor, this method gives a value which indicates how much longer the skin protected with the light protection composition can be irradiated with UV-A radiation until the pigmentation which occurs is the same as for the unprotected skin.

Another test method which has become established throughout Europe is the Australian Standard AS/NZS 2604:1997. Here, the absorption of the preparation in the UV-A region is measured. In order to satisfy the standard, the preparation must absorb at least 90% of the UV-A radiation in the region 320–360 nm.

The use concentration of known light protection filter substances which, in particular, also exhibit high filter action in the UV-A region is often limited by the very fact that they are combined with other substances which are in the form of solids. There are therefore certain formulation difficulties in achieving relatively high light protection factors or UV-A protection performance.

Since light protection filter substances are usually expensive and since some light protection filter substances are additionally difficult to incorporate in relatively high concentrations into cosmetic or dermatological preparations, an object of the invention was to obtain, in a simple and cost-effective manner, preparations which, despite having an unusually low concentration of conventional UV-A light protection filter substances, nevertheless achieve acceptable or even high UV-A protection performance.

UV radiation can, however, also lead to photochemical reactions, in which case the photochemical reaction products intervene in the skin's metabolism. Such photochemical reaction products are predominantly free-radical compounds, for example hydroxyl free radicals. Undefined free-radical photoproducts which form in the skin itself can also display uncontrolled secondary reactions because of their high reactivity. However, singlet oxygen, a non-free-radical excited state of the oxygen molecule, can also be formed during UV irradiation, as can short-lived epoxides and many others. Singlet oxygen, for example, differs from normal triplet oxygen (free-radical ground state) by virtue of its increased reactivity. However, excited, reactive (free-radical) triplet states of the oxygen molecule also exist.

In order to prevent these reactions, it is possible additionally to incorporate antioxidants and/or free-radical scavengers into the cosmetic or dermatological formulations.

Known and advantageous light protection filter substances are dibenzoylmethane derivatives, for example 5-isopropyidibenzoylmethane (CAS No. 63250-25-9), and also 4-(tert-butyl)4'-methoxydibenzoylmethane (CAS No. 70356-09-1). However, precisely because they are in combination with other substances which are in the form of solids, their use concentration is limited. There are therefore certain formulation difficulties in achieving relatively high light protection factors.

Another advantageous light protection filter substance is 4-methylbenzylidenecamphor. This is an extremely advantageous light protection filter substance, which is solid under normal conditions and is notable per se for good UV filter properties. However, precisely because of its combination with other substances which are in the form of solids, its use concentration too is limited. There are therefore certain formulation difficulties in achieving relatively high light protection factors here as well.

Another advantageous UV filter is 2,4-bis-{[4-(2-ethylhexyloxy)-2-hydroxy]phenyl}-6-(4-methoxyphenyl)-1,3,5-triazine, which is characterized by the following structure:

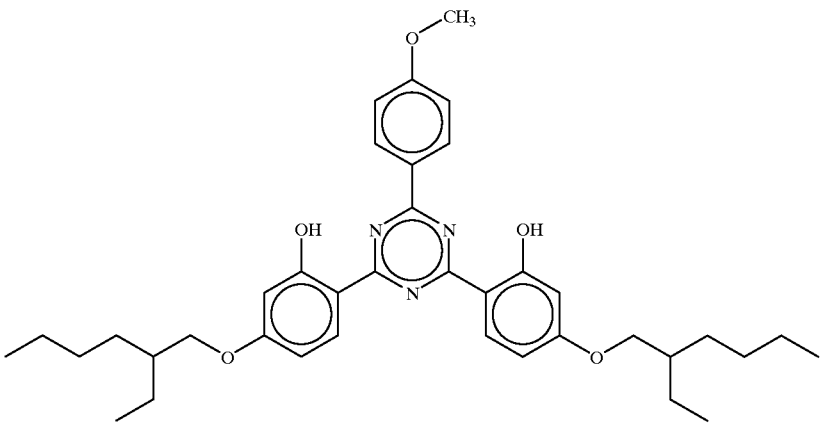

This UV filter substance is marketed by Ciba Specialty Chemicals Holding Inc. under the trade name Tinosorb® S and is characterized by good UV absorption properties.

The main disadvantage of 2,4-bis-{[4-(2-ethylhexyloxy)-2-hydroxy]phenyl}-6-(4-methoxyphenyl)-1,3,5-triazine is its poor solubility in lipids. Known solvents for this UV filter can dissolve a maximum of about 10% by weight of this filter, corresponding to about 1% by weight of dissolved, and thus active, UV filter substance in light protection preparations.

There are therefore certain formulation difficulties in achieving relatively high light protection factors here as well.

The light protection factor (LPF, often also known as SPF for sun protection factor) indicates how much longer the skin protected with the light protection composition can be irradiated until the erythema reaction which occurs is the same as for the unprotected skin (i.e. 10 times longer compared with unprotected skin for LPF=10).

In any case, the consumer expects, on the one hand, reliable information from the manufacturer regarding the light protection factor—not least because of the discussion about the "hole in the ozone layer" which has become a topic of public interest, and on the other hand there is a tendency by the consumer towards relatively high and high light protection factors.

Since light protection filter substances are usually expensive, and since some light protection filter substances are also difficult to incorporate into cosmetic or dermatological preparations in relatively high concentrations, a further object of the invention was to obtain, in a simple and cost-effective manner, preparations which, despite having unusually low concentrations of conventional light protection filter substances, nevertheless achieve acceptable or even high LPF values.

Another light protection filter substance which can additionally be used advantageously according to the invention is ethylhexyl 2-cyano-3,3-diphenylacrylate (octocrylene), which is available from BASF under the name UVINUL® N 539 and is characterized by the following structure:

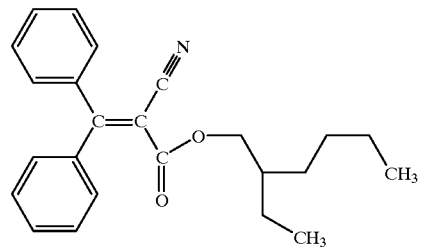

It was therefore surprising and could not have been foreseen by the person skilled in the art that the use of ethylhexyl 2-cyano-3,3-diphenylacrylate for solubilizing 2,4-bis-{[4-(2-ethylhexyloxy)-2-hydroxy]phenyl}-6-(4-methoxyphenyl)-1,3,5-triazine in cosmetic or dermatological light protection compositions overcomes the disadvantages of the prior art.

It was also surprising that the addition of octocrylene effects stabilization of solutions of 2,4-bis-{[4-(2-ethylhexyloxy)-2-hydroxy]phenyl}-6-(4-methoxyphenyl)-1,3,5-triazine, since the latter substance not only has poor solubility, but also readily recrystallizes from its solution.

The invention also therefore relates to a method of stabilizing solutions of 2,4-bis-{[4-(2-ethylhexyloxy-2-hydroxy]phenyl}-6-(4-methoxyphenyl)-1,3,5-triazine, characterized in that an effective content of octocrylene is added to such solutions.

It was further surprising that the use of octocrylene for increasing the light protection factor and/or the UV-A protection performance of cosmetic or dermatological preparations which comprise 2,4-bis-{[4-(2-ethylhexyloxy)-2-hydroxy]phenyl}-6-(4-methoxyphenyl)-1,3,5-triazine and the use of 2,4-bis-{[4-(2-ethylhexyloxy)-2-hydroxy]phenyl}-6-(4-methoxyphenyl)-1,3,5-triazine for increasing the light protection factor and/or the UV-A protection performance of cosmetic or dermatological preparations which comprise octocrylene overcome the disadvantages of the prior art.

The total amount of 2,4-bis-{[4-(2-ethylhexyloxy)-2-hydroxy]phenyl}-6-(4-methoxyphenyl)-1,3,5-triazine in the finished cosmetic or dermatological preparations is advantageously chosen from the range 0.1–10.0% by weight, preferably 0.5–6.0% by weight, based on the total weight of the preparations.

The total amount of octocrylene in the finished cosmetic or dermatological preparations is advantageously chosen from the range 0.1–25.0% by weight, preferably 0.5–15.0% by weight, based on the total weight of the preparations.

It is advantageous to choose weight ratios of 2,4-bis-{[4-(2-ethylhexyloxy)-2-hydroxy]phenyl}-6-(4-methoxyphenyl)-1,3,5-triazine and octocrylene from the range from 1:10 to 10:1, preferably from 1:4 to 4:1.

Cosmetic and dermatological preparations according to the invention further advantageously comprise inorganic pigments based on metal oxides and/or other metal compounds which are virtually insoluble or insoluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and mixtures of such oxides. The pigments are particularly preferably those based on $TiO_2$.

For the purposes of the present invention, it is particularly advantageous, although not obligatory, for the inorganic pigments to be present in hydrophobic form, i.e. to have been surface-treated to repel water. This surface treatment may involve providing the pigments with a thin hydrophobic layer by processes known per se.

Such a process involves, for example, producing the hydrophobic surface layer by a reaction according to

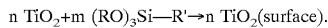
$$n\ TiO_2 + m\ (RO)_3Si\text{—}R' \rightarrow n\ TiO_2(\text{surface}).$$

n and m are stoichiometric parameters to be employed here as desired, and R and R' are the desired organic radicals. Hydrophobicized pigments prepared analogously to DE-A 33 14 742, for example, are advantageous.

Advantageous $TiO_2$ pigments are obtainable, for example, under the trade names MT 100 T from TAYCA, M 160 from Kemira and T 805 from Degussa.

The cosmetic and/or dermatological light protection formulations according to the invention can have the customary composition and can be used for cosmetic and/or dermatological light protection, and also for the treatment, care and cleansing of the skin and/or hair, and as a make-up product in decorative cosmetics.

For use, the cosmetic and dermatological preparations according to the invention are applied to the skin and/or the hair in an adequate amount in the manner customary for cosmetics.

Particular preference is given to cosmetic and dermatological preparations which are in the form of a sunscreen. These can advantageously additionally comprise at least one further UV-A filter and/or at least one further UV-B filter and/or at least one inorganic pigment, preferably an inorganic micropigment.

The cosmetic and dermatological preparations according to the invention can comprise cosmetic auxiliaries as are customarily used in such preparations, for example preservatives, bactericides, perfumes, antifoams, dyes, pigments which have a colouring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

An additional content of antioxidants is generally preferred. According to the invention, favourable antioxidants which can be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones, penta-, hexa- and hepta-thionine-sulphoximine) in very low tolerated doses (for example pmol to μmol/kg), and furthermore (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, furfurylidenesorbitol and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof is or are the antioxidant or antioxidants, it is advantageous to choose the respective concentrations thereof from the range 0.001–10% by weight, based on the total weight of the formulation.

If vitamin A or vitamin A derivatives or carotenes or derivatives thereof is or are the antioxidant or antioxidants, it is advantageous to choose the respective concentrations thereof from the range 0.001–10% by weight, based on the total weight of the formulation.

The lipid phase can advantageously be chosen from the following group of substances:

mineral oils, mineral waxes oils, such as triglycerides of capric or of caprylic acid fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids;

alkyl benzoates;

silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyidodecyl palmitate, oleyl oleate, oleyl erucate, erucyl oleate, erucyl erucate and also synthetic, semisynthetic and natural mixtures of such esters, e.g. jojoba oil.

In addition, the oil phase can advantageously be chosen from the group of branched and unbranched hydrocarbons and hydrocarbon waxes, silicone oils, dialkyl ethers, the group of saturated or unsaturated, branched or unbranched alcohols, and also fatty acid triglycerides, specifically the triglyceryl ester of saturated and/or unsaturated, branched and/or unbranched alkanecarboxylic acids having a chain length of from 8 to 24, in particular 12–18 carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and more of the same type.

Any desired mixtures of such oil and wax components can also be advantageously used for the purposes of the present invention. It may also be advantageous in some circumstances to use waxes, for example cetyl palmitate, as the sole lipid. component of the oil phase.

The oil phase is advantageously chosen from the group consisting of 2-ethylhexyl isostearate, octyidodecanol, isotridecyl isononanoate, isoeicosane, 2-ethylhexyl cocoate, $C_{12-15}$-alkyl benzoate, caprylic-capric acid triglyceride and dicaprylyl ether.

Particularly advantageous mixtures are those of C12-15-alkyl benzoate and 2-ethylhexyl isostearate, mixtures of $C_{12-15}$-alkyl benzoate and isotridecyl isononanoate and also mixtures of $C_{12-15}$-alkyl benzoate, 2-ethylhexyl isostearate and isotridecyl isononanoate.

Of the hydrocarbons, paraffin oil, squalane and squalene are advantageous for the purposes of the present invention.

The oil phase may also advantageously contain cyclic or linear silicone oils or consist entirely of such oils, preference, however, being given to using, as well as the silicone oil or the silicone oils, an additional content of other oil phase components.

Cyclomethicone (octamethylcyclotetrasiloxane) is advantageously employed as the silicone oil to be used according to the invention. However, other silicone oils are also advantageous for the purposes of the present invention, for example hexamethylcyclotrisiloxane, polydimethylsiloxane and poly(methylphenylsiloxane).

Other particularly advantageous mixtures comprise cyclomethicone and isotridecyl isononanoate, and cyclomethicone and 2-ethylhexyl isostearate.

If appropriate, the aqueous phase of the preparations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the Carbopol group, for example Carbopols of grades 980, 981, 1382, 2984 and 5984, each individually or in combination.

The cosmetic or dermatological light protection preparations advantageously comprise inorganic pigments, in particular micropigments, e.g. in amounts from 0.1% by weight to 30% by weight, preferably in amounts from 0.5% by weight to 10% by weight, but in particular from 1% by weight to 6% by weight, based on the total weight of the preparations.

For the purposes of the invention, cosmetic and dermatological formulations advantageously comprise one or more customary UV-A filters as individual substances or in any mixtures with one another, in the lipid phase and/or in the aqueous phase.

The total amount of UV-A filter substances in the finished cosmetic or dermatological preparations is advantageously chosen from the range from 0.1 to 30% by weight, preferably from 0.1 to 10.0% by weight, in particular from 0.5 to 5.0% by weight, based on the total weight of the preparations.

Cosmetic and dermatological preparations according to the invention advantageously comprise, although this is not obligatory, further inorganic pigments which may be X-ray-amorphous or non-X-ray-amorphous.

X-ray-amorphous oxide pigments are metal oxides or semimetal oxides which reveal no or no recognizable crystal structure in X-ray diffraction experiments. Such pigments are often obtainable by flame reaction, for example by reacting a metal or semimetal halide with hydrogen and air (or pure oxygen) in a flame.

In cosmetic, dermatological or pharmaceutical formulations according to the invention, X-ray-amorphous oxide pigments are advantageously used as thickeners and thixotropic agents, flow auxiliaries, for emulsion and dispersion stabilization and as a carrier substance (for example to increase the volume of finely divided powders), but they can also be used to increase the light protection performance.

Known X-ray-amorphous oxide pigments which can be used advantageously in preparations according to the invention are the silicon oxides of the Aerosil® type (CAS-No. 7631-86-9). Aerosils®), obtainable from DEGUSSA, are characterized by a small particle size (e.g. between 5 and 40 nm), the particles being regarded as spherical particles of very uniform dimension. Macroscopically, Aerosils® are recognizable as loose, white powders. For the purposes of the present invention, X-ray-amorphous silicon dioxide pigments are particularly advantageous and, of these, it is precisely those of the Aerosil® type which are preferred.

Advantageous Aerosil® types are, for example, Aerosil® OX50, Aerosil® 130, Aerosil® 150, Aerosil® 200, Aerosil®

300, Aerosil® 380, Aerosil® MOX 80, Aerosil® 170, Aerosil® COK 84, Aerosil® R 202, Aerosil® R 805, Aerosil® R 812, Aerosil® R 972, Aerosil® R 974, Aerosil® R 976.

According to the invention it is advantageous, although not obligatory, for cosmetic or dermatological light protection preparations to comprise from 0.1 to 20% by weight, preferably from 0.5 to 10% by weight, very particularly preferably from 1 to 5% by weight, of X-ray-amorphous oxide pigments.

It is also advantageous according to the invention for preparations to comprise inorganic pigments, in particular micropigments, which are non-X-ray-amorphous, based on metal oxides and/or other metal compounds which are virtually insoluble or insoluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals, and mixtures of such oxides. Particular preference is given to pigments based on $TiO_2$.

Pigments of this type shield UV radiation, including UV-A radiation, and are to be regarded as UV filter substances for the purposes of the present invention.

According to the invention, the non-X-ray-amorphous inorganic pigments are advantageously in hydrophobic form, i.e. have been surface-treated to repel water. This surface treatment may involve providing the pigments with a thin, hydrophobic layer by processes known per se.

Such a method involves, for example, producing the hydrophobic surface layer by a reaction according to

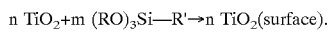

n $TiO_2$+m $(RO)_3Si$—R'→n $TiO_2$(surface).

n and m are stoichiometric parameters to be employed as desired, and R and R' are the desired organic radicals. Hydrophobicized pigments prepared analogously to DE-A 33 14 742, for example, are advantageous.

Advantageous $TiO_2$ pigments are obtainable, for example, under the trade name T 805 from Degussa.

The total amount of inorganic pigments, in particular hydrophobic inorganic micro-pigments, in the finished cosmetic or dermatological preparations is advantageously chosen from the range 0.1–30% by weight, preferably 0.1–10.0% by weight, in particular 0.5–6.0% by weight, based on the total weight of the preparations.

The cosmetic and/or dermatological light protection formulations according to the invention can have the customary composition and can be used for cosmetic and/or dermatological light protection, and also for the treatment, care and cleansing of the skin and/or the hair, and as a make-up product in decorative cosmetics.

For use, of the cosmetic and dermatological preparations according to the invention are applied to the skin and/or hair in an adequate amount in the manner customary for cosmetics.

Particular preference is given to cosmetic or dermatological preparations which are in the form of a sunscreen. These can advantageously additionally comprise at least one further UV-A filter and/or at least one further UV-B filter and/or at least one inorganic pigment, preferably an inorganic micropigment.

Such UV-B filters can be oil-soluble or water-soluble. Advantageous oil-soluble UV-B filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

2,4,6-trianilino(p-carbo-2'-ethyl-1'-hexyloxy)-1,3,5-triazine;

dioctylbutamidotriazone, esters of benzalmalonic acid, preferably di(2-ethylhexyl) 4-methoxybenzalmalonate;

esters of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone.

Advantageous water-soluble UV-B filter substances are, for example:

salts of 2-phenylbenzimidazole-5-sulphonic acid, such as its sodium, potassium or its triethanolammonium salt, and the sulphonic acid itself;

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl) sulphonic acid and salts thereof.

The list of UV-B filters mentioned which can additionally be used for the purposes of the present invention is not of course intended to be limiting.

According to the invention, advantageous preparations are characterized in that the cosmetic or dermatological light protection preparations comprise, as UV-A filter substance, one or more water-soluble UV-A filter substances, particularly water-soluble UV-A filter substances chosen from the group consisting of phenylene-1,4-bis-(2-benzimidazyl)-3,3',5,5'-tetrasulphonic acid and/or 1,4-di(2-oxo-10-sulpho-3-bornylidenemethyl)benzene and/or salts thereof, particularly the corresponding sodium, potassium or triethanolammonium salts and/or the corresponding 10-sulphato compounds, in particular the bis-sodium salt of phenylene-1,4-bis-(2-benzimidazyl)-3,3',5,5'-tetrasulphonic acid.

According to the invention, further advantageous preparations are characterized in that the cosmetic or dermatological light protection preparations comprise, as UV-A filter substance, one or more oil-soluble UV-A filter substances, in particular chosen from the group of dibenzoylmethane derivates, for example 5-isopropyidibenzoylmethane, and 4 (tert-butyl)4'-methoxydibenzoylmethane.

It can also be considerably advantageous to use polymer-bound or polymeric UV filter substances in preparations according to the present invention, in particular those described in WO-A-92/20690.

According to the invention, therefore, advantageous preparations are also those comprising polymer-bound or polymeric UV filter substances, the total amount of such filter substances being, for example, from 0.1% by weight to 30% by weight, preferably from 0.5 to 20% by weight, in particular from 3 to 15% by weight, based on the total weight of the preparations.

The total amount of water-soluble UV filter substances in the finished cosmetic or dermatological preparations according to the invention is advantageously chosen from the range 0.1–10.0% by weight, preferably 0.5–6.0% by weight, based on the total weight of the preparations.

The total amount of oil-soluble UV filter substances in the finished cosmetic or dermatological preparations according to the invention is advantageously chosen from the range 0.1–30.0% by weight, preferably 0.5–15.0% by weight, based on the total weight of the preparations.

The total amount of 2-phenylbenzimidazole-5-sulphonic acid or its salts in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of 2-hydroxy4-methoxybenzophenone-5-sulphonic acid or its salts in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of 4-(2-oxo-3-bornylidenemethyl)benzenesulphonic acid or its salts in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of 2-methyl-5-(2-oxo-3-bornylidenemethyl)benzenesulphonic acid or its salts in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of benzene-1,4-di(2-oxo-3-bornylidenemethyl)-10-sulphonic acid or its salts in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of tris(2-ethylhexyl) 4,4',4''-(1,3,5-triazine-2,4,6-triyltriimino)tris-benzoate in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of 4-(tert-butyl)-4'-methoxydibenzoylmethane in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of 4-methylbenzylidenecamphor in the finished cosmetic or dermatological preparations according to the invention is, in cases where the presence of this substance is desired, advantageously chosen from the range 0.1–10.0% by weight, preferably 0.5–6.0% by weight, based on the total weight of the preparations.

The total amount of 2-ethylhexyl p-methoxycinnamate in the finished cosmetic or dermatological preparations according to the invention is, in cases where the presence of this substance is desired, advantageously chosen from the range 0.1–15.0% by weight, preferably 0.5–7.5% by weight, based on the total weight of the preparations.

According to the invention, it may also in some circumstances be advantageous to incorporate other UV-A and/or UV-B filters into cosmetic or dermatological preparations, for example certain salicylic acid derivatives, such as 4-isopropylbenzyl salicylate, 2-ethylhexyl salicylate (=octyl salicylate), and homomenthyl salicylate.

According to the invention, the total amount of one or more salicylic acid derivatives in the finished cosmetic or dermatological preparations is advantageously chosen from the range 0.1–15.0% by weight, preferably 0.5–8.0% by weight, based on the total weight of the preparations. If ethylhexyl salicylate is chosen, it is advantageous to choose its total amount from the range 0.1–5.0% by weight, preferably 0.5–2.5% by weight. If homomenthyl salicylate is chosen, it is advantageous to choose its total amount from the range 0.1–10.0% by weight, preferably 0.5–5.0% by weight.

The invention also relates to a process for the preparation of the cosmetic and/or dermatological light protection preparations according to the invention, which is characterized in that 2,4-bis-{[4-(2-ethylhexyloxy)-2-hydroxy]phenyl}-6-(4-methoxyphenyl)-1,3,5-triazine is suspended in a manner known per se in octocrylene or an oil phase containing octocrylene with uniform stirring and optionally with heating, and, if desired, homogenized, optionally combined with further lipid components and optionally with one or more emulsifiers, after which the oil phase is mixed with the aqueous phase, into which a thickener has optionally been incorporated, and which preferably has the same temperature as the oil phase, if desired homogenized and left to cool to room temperature. Following cooling to room temperature, homogenization can be repeated, particularly if constituents which are still volatile are to incorporated.

The examples below are intended to illustrate the present invention without limiting it. Unless stated otherwise, all quantities, proportions and percentages are based on the weight and the total amount or on the total weight of the preparations.

EXAMPLE 1

| O/W emulsion | % by weight |
|---|---|
| Stearic acid | 1.50 |
| Glycerol monostearate | 3.00 |
| Caprylic/capric triglyceride | 10.00 |
| Dicaprylyl ether | 5.00 |
| Dimethicone | 2.00 |
| Hydrogenated polyisobutene | 2.00 |
| Vitamin E acetate | 0.50 |
| Octocrylene | 10.00 |
| Tinosorb ® S | 4.00 |
| Methylbenzylidenecamphor | 4.00 |
| Titanium dioxide | 1.00 |
| Preservative | q.s. |
| Glycerol | 3.00 |
| Xanthan gum | 0.30 |
| Sodium hydroxide solution, 45% | 0.50 |
| Water | ad 100.00 |

EXAMPLE 2

| O/W emulsion | % by weight |
|---|---|
| Sorbitan stearate | 3.00 |
| Polyglyceryl-3 methylglucose distearate | 1.50 |
| Octyldodecanol | 10.00 |
| Dicaprylyl ether | 5.00 |
| Mineral oil | 5.00 |
| Castor oil | 2.00 |
| Butylene glycol dicaprylate/caprate | 5.00 |
| Vitamin E acetate | 0.50 |
| Octocrylene | 8.00 |
| Tinosorb ® S | 1.50 |
| Octyltriazone | 4.00 |
| Methylbenzylidenecamphor | 4.00 |

-continued

| O/W emulsion | % by weight |
|---|---|
| Butylmethoxydibenzoylmethane | 3.00 |
| Preservative | q.s. |
| Glycerol | 10.00 |
| Xanthan gum | 0.20 |
| Pemulen ®TR1 | 0.10 |
| Phenylbenzimidazolesulphonic acid | 2.00 |
| Sodium hydroxide solution, 45% | 1.20 |
| Water | ad 100.00 |

EXAMPLE 3

| W/O emulsion | % by weight |
|---|---|
| Polyglyceryl-2 dipolyhydroxystearate | 5.00 |
| Dimethicone | 2.00 |
| Mineral oil | 5.00 |
| Isohexadecane | 5.00 |
| Butylene glycol dicaprylate/caprate | 5.00 |
| Dioctylbutamidotriazone | 3.00 |
| Octocrylene | 12.00 |
| Tinosorb ® S | 3.00 |
| Methylbenzylidenecamphor | 2.00 |
| Butylmethoxydibenzoylmethane | 2.00 |
| Titanium dioxide | 4.00 |
| Preservative | q.s. |
| Glycerol | 5.00 |
| $MgSO_4$ | 1.00 |
| Water | ad 100.00 |

EXAMPLE 4

| W/O emulsion | % by weight |
|---|---|
| PEG-30 dipolyhydroxystearate | 4.00 |
| Caprylic/capric triglyceride | 5.00 |
| Octyldodecanol | 5.00 |
| Dicaprylyl ether | 5.00 |
| Mineral oil | 5.00 |
| Hydrogenated polyisobutene | 5.00 |
| Vitamin E acetate | 0.50 |
| Dioctylbutamidotriazone | 1.00 |
| Octocrylene | 6.00 |
| Tinosorb ® S | 2.00 |
| Aerosil ® R972 | 0.50 |
| Preservative | 0.50 |
| Glycerol | 10.00 |
| $MgSO_4$ | 1.00 |
| Water | ad 100.00 |

EXAMPLE 5

| W/O emulsion | % by weight |
|---|---|
| Cetyldimethicone copolyol | 5.00 |
| Dimethicone | 5.00 |
| Mineral oil | 2.00 |
| Isohexadecane | 2.00 |

-continued

| W/O emulsion | % by weight |
|---|---|
| $C_{12-15}$-alkyl benzoate | 5.00 |
| Octocrylene | 15.00 |
| Tinosorb ® S | 6.00 |
| Methylbenzylidenecamphor | 400 |
| Butylmethoxydibenzoylmethane | 2.00 |
| Titanium dioxide | 2.00 |
| Preservative | q.s. |
| Glycerol | 5.00 |
| NaCl | 1.00 |
| Phenylbenzimidazolesulphonic acid | 4.00 |
| Sodium hydroxide solution, 45% | 1.30 |
| Water | ad 100.00 |

EXAMPLE 6

| Hydrodispersion | % by weight |
|---|---|
| Caprylic/capric triglyceride | 10.00 |
| Octyldodecanol | 5.00 |
| Dicaprylyl ether | 2.00 |
| Dimethicone | 1.00 |
| Vitamin E acetate | 0.50 |
| Octyltriazone | 2.00 |
| Methylbenzylidenecamphor | 4.00 |
| Butylmethoxydibenzoylmethane | 2.00 |
| Titanium dioxide | 1.00 |
| Preservative | q.s. |
| Glycerol | 3.00 |
| Xanthan gum | 0.40 |
| Pemulen ®TR1 | 0.40 |
| Sodium hydroxide solution, 45% | 0.40 |
| Water | ad 100.00 |

EXAMPLE 7

| W/O Pickering emulsion | % by weight |
|---|---|
| Caprylic/capric triglyceride | 15.00 |
| Hydrogenated polyisobutene | 5.00 |
| $C_{12-15}$-alkyl benzoate | 5.00 |
| Octocrylene | 10.00 |
| Tinosorb ® S | 4.00 |
| Titanium dioxide | 4.00 |
| Aerosil ® R972 | 2.00 |
| Preservative | 0.50 |
| Glycerol | 5.00 |
| NaCl | 1.00 |
| Phenylbenzimidazolesulphonic acid | 1.00 |
| Sodium hydroxide solution, 45% | 0.40 |
| Water | ad 100.00 |

EXAMPLE 8

| Spray | |
|---|---|
| | % by weight |
| Glycerol monostearate | 4.00 |
| Ceteareth-12 | 1.50 |
| Caprylic/capric triglyceride | 2.00 |
| Mineral oil | 5.00 |
| Octocrylene | 6.00 |
| Tinosorb ® S | 3.00 |
| Octyltriazone | 1.00 |
| Preservative | q.s. |
| Glycerol | 10.00 |
| Phenylbenzimidazolesulphonic acid | 1.00 |
| Sodium hydroxide solution, 45% | 0.40 |
| Water | ad 100.00 |

EXAMPLE 9

| Spray | |
|---|---|
| | % by weight |
| Glycerol monostearate SE | 4.50 |
| Ceteareth-20 | 1.00 |
| Dicaprylyl ether | 5.00 |
| Cetearyl isononanoate | 5.00 |
| Dimethicone | 2.00 |
| Octocrylene | 8.00 |
| Tinosorb ® S | 4.00 |
| Preservative | q.s. |
| Glycerol | 5.00 |
| Water | ad 100.00 |

What is claimed is:

1. A method of solubilizing a content of 2,4-bis-{[4-(2-ethylhexyloxy- 2-hydroxy]phenyl}-6-(4-methoxyphenyl)-1,3,5-triazine in a cosmetic or dermatological composition, said method comprising adding to said cosmetic or dermatological composition a content of ethylhexyl 2-cyano-3,3-diphenylacrylate (octocrylene) sufficient to solubilize the content of 2,4-bis-{[4-(2-ethylhexyloxy)-2-hydroxy]phenyl}-6-(4-methoxyphenyl)-1,3,5-triazine.

2. The method according to claim 1, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.1 to 10.0% by weight based on the total weight of the cosmetic or dermatological composition.

3. The method according to claim 2, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.5 to 6.0% by weight based on the total weight of the cosmetic or dermatological composition.

4. The method according to claim 1, wherein the content of octocrylene in the cosmetic or dermatological composition ranges from 0.1 to 25.0% by weight based on the total weight of the cosmetic or dermatological composition.

5. The method according to claim 4, wherein the content of octocrylene in the cosmetic or dermatological composition ranges from 0.5 to 15.0% by weight based on the total weight of the cosmetic or dermatological composition.

6. A method of increasing the light protection factor and/or the UV-A protection performance of a cosmetic or dermatological composition comprising a content of 2,4-bis-{[4-(2-ethylhexyloxy)-2-hydroxy]phenyl}-6-(4-methoxyphenyl)-1,3,5-triazine, said method comprising adding to said cosmetic or dermatological composition a content of ethylhexyl 2-cyano-3,3-diphenylacrylate (octocrylene) sufficient to increase the light protection factor and/or the UV-A protection performance of said cosmetic or dermatological composition.

7. The method according to claim 6, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.1 to 10.0% by weight based on the total weight of the cosmetic or dermatological composition.

8. The method according to claim 7, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.5 to 6.0% by weight based on the total weight of the cosmetic or dermatological composition.

9. The method according to claim 6, wherein the content of octocrylene in the cosmetic or dermatological composition ranges from 0.1 to 25.0% by weight based on the total weight of the cosmetic or dermatological composition.

10. The method according to claim 9, wherein the content of octocrylene in the cosmetic or dermatological composition ranges from 0.5 to 15.0% by weight based on the total weight of the cosmetic or dermatological composition.

11. A method of increasing the light protection factor and/or the UV-A protection performance of a cosmetic or dermatological composition comprising a content of ethylhexyl 2-cyano-3,3-diphenylacrylate (octocrylene), said method comprising adding to said cosmetic or dermatological composition a content of 2,4-bis-{[4-(2-ethylhexyloxy)-2-hydroxy]phenyl}-6-(4-methoxyphenyl)-1,3,5-triazine sufficient to increase the light protection factor and/or the UV-A protection performance of said cosmetic or dermatological composition.

12. The method according to claim 11, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.1 to 10.0% by weight based on the total weight of the cosmetic or dermatological composition.

13. The method according to claim 12, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.5 to 6.0% by weight based on the total weight of the cosmetic or dermatological composition.

14. The method according to claim 11, wherein the content of octocrylene in the cosmetic or dermatological composition ranges from 0.1 to 25.0% by weight based on the total weight of the cosmetic or dermatological composition.

15. The method according to claim 14, wherein the content of octocrylene in the cosmetic or dermatological composition ranges from 0.5 to 15.0% by weight based on the total weight of the cosmetic or dermatological composition.

16. A cosmetic or dermatological composition comprising:
   a) a content of 2,4-bis-{[4-(2-ethylhexyloxy)-2-hydroxy]phenyl}-6-(4-methoxyphenyl)-1,3,5-triazine; and
   b) a content of ethylhexyl 2-cyano-3,3-diphenylacrylate (octocrylene) sufficient to solubilize said content of 2,4-bis-{[4-( 2-ethylhexyloxy)-2-hydroxy]phenyl}-6-(4-methoxyphenyl)-1,3,5-triazine.

17. The cosmetic or dermatological composition according to claim 16, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.1 to 10.0% by weight based on the total weight of the cosmetic or dermatological composition.

18. The cosmetic or dermatological composition according to claim 17, wherein the content of 2,4-bis-{[4-(2-ethylhexyloxy)-2-hydroxy]phenyl}-6-(4-methoxyphenyl)-1,3,5-triazine in the cosmetic or dermatological composition ranges from 0.5 to 6.0% by weight based on the total weight of the cosmetic or dermatological composition.

19. The cosmetic or dermatological composition according to claim 16, wherein the content of octocrylene in the cosmetic or dermatological composition ranges from 0.1 to 25.0% by weight based on the total weight of the cosmetic or dermatological composition.

20. The cosmetic or dermatological composition according to claim 19, wherein the content of octocrylene in the cosmetic or dermatological composition ranges from 0.5 to 15.0% by weight based on the total weight of the cosmetic or dermatological composition.

* * * * *

UNITED STATES PATENT AND TRADEMARK OFFICE
CERTIFICATE OF CORRECTION

PATENT NO.   : 6,423,302 B1
DATED        : July 23, 2002
INVENTOR(S)  : Heinrich Gers-Barlag and Anja Muller It is certified that error appears in the above-identified patent and that said Letters Patent is hereby corrected as shown below:

<u>Column 15,</u>
Line 38, delete "ethylhexyloxy-2-" and substitute -- ethylhexyloxy)-2- --

Signed and Sealed this

Fourth Day of March, 2003

JAMES E. ROGAN
*Director of the United States Patent and Trademark Office*